United States Patent
Kawashima et al.

(10) Patent No.: US 7,422,870 B2
(45) Date of Patent: Sep. 9, 2008

(54) BACTERIA COUNTING METHOD

(75) Inventors: Yasuyuki Kawashima, Kobe (JP); Yoshiro Ikeuchi, Kobe (JP); Yasuhiro Sakai, Kobe (JP)

(73) Assignee: Sysmex Corporation, Kobe (JP)

( * ) Notice: Subject to any disclaimer, the term of this patent is extended or adjusted under 35 U.S.C. 154(b) by 338 days.

(21) Appl. No.: 10/679,146

(22) Filed: Oct. 3, 2003

(65) Prior Publication Data

US 2004/0067548 A1   Apr. 8, 2004

(30) Foreign Application Priority Data

Oct. 4, 2002   (JP)   ............................. 2002-292606

(51) Int. Cl.
  *C12Q 1/04*   (2006.01)
(52) U.S. Cl. ........................................................ 435/34
(58) Field of Classification Search .................... 435/34
  See application file for complete search history.

(56) References Cited

U.S. PATENT DOCUMENTS

| | | | | |
|---|---|---|---|---|
| 4,665,024 | A * | 5/1987 | Mansour | 435/34 |
| 5,545,535 | A * | 8/1996 | Roth et al. | 435/34 |
| 7,309,581 | B2 * | 12/2007 | Sakai et al. | 435/40.5 |
| 2004/0142398 | A1 * | 7/2004 | Bandla et al. | 435/7.32 |
| 2004/0175781 | A1 * | 9/2004 | Sakai et al. | 435/34 |
| 2005/0042744 | A1 * | 2/2005 | Kawashima | 435/288.7 |

FOREIGN PATENT DOCUMENTS

| | | |
|---|---|---|
| EP | 1 136 563 A2 | 9/2001 |
| EP | 1 203 825 A2 | 5/2002 |

OTHER PUBLICATIONS

Roth, Bruce L.; Poot, Martin; Yue, Stephen T.; Millard, Paul J. "Bacterial Viability and Antibiotic Susceptibility Testing with SYTOX Green Nucleic Acid Stain", *Applied and Environmental Microbiology*, 1997, 63, 2421-2431.

Suller, M.T.E.; Lloyd, D. "Fluorescence Monitoring of Antibiotic-Induced Bacterial Damage Using Flow Cytometry", *Cytometry*, 1999, 35, 235-241.

XP-002270007 Abstract of SU 1306947 A, V.S. Bannikov, Apr. 30, 1987.

* cited by examiner

*Primary Examiner*—Jon P Weber
*Assistant Examiner*—Kailash C Srivastava
(74) *Attorney, Agent, or Firm*—Brinks Hofer Gilson & Lione

(57) ABSTRACT

Methods for counting bacteria are described that include: (a) preparing an assay sample by staining a specimen using a fluorescent dye, thereby producing a difference in fluorescent intensity between live bacteria and dead bacteria; (b) detecting optical information from the assay sample; and (c) classifying and counting the live bacteria and the dead bacteria based on the detected optical information. Bacteria counting apparatuses and reagent kits for counting bacteria are also described.

9 Claims, 12 Drawing Sheets

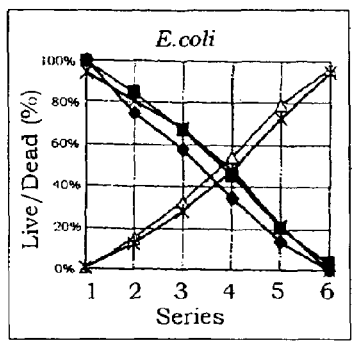

- ♦ Live Bacteria%(agar culture method)
- ■ Live Bacteria%(method of example 3 of this invention)
- △ Dead Bacteria%(method of example 3 of this invention)
- ✳ Live Bacteria%(Baclight)
- ✳ Dead Bacteria%(Baclight)

*Fig. 10A*

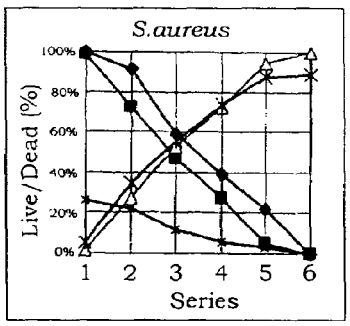

- ♦ Live Bacteria%(agar culture method)
- ■ Live Bacteria%(method of example 3 of this invention)
- △ Dead Bacteria%(method of example 3 of this invention)
- ✳ Live Bacteria%(Baclight)
- ✳ Dead Bacteria%(Baclight)

*Fig 10B*

—◆— Live Bacteria%(agar culture method)
—■— Live Bacteria%(method of example 3 of this invention)
—△— Dead Bacteria%(method of example 3 of this invention)
—✕— Live Bacteria%(Baclight)
—✳— Dead Bacteria%(Baclight)

— Total Bacteria Count obtained from the assay sample II
— Live Bacteria Count obtained from the assay sample I and II
— Live Bacteria Count obtained by Baclight
— Live Bacteria Count obtained by agar culture method
— Total Bacteria Count obtained from the assay sample III

BACTERIA COUNTING METHOD

RELATED APPLICATIONS

This application claims priority to Japanese Patent Application No. 2002-292606, filed Oct. 4, 2002.

BACKGROUND

The present invention relates to bacteria counting methods, bacteria counting apparatuses, and bacteria counting reagent kits. More particularly, the present invention relates to bacteria counting methods, bacteria counting apparatuses, and bacteria counting reagent kits for classifying and counting dead bacteria and live bacteria using fluorescent dyes.

Counting the number of bacteria contained in specimens of living organisms or food sources in order to determine whether or not bacteria exist in the food or living organisms is performed in the fields of clinical examinations and food sanitation inspections. Conventional counting methods include culturing, ATP assays, and fluorescent assay methods.

The culturing method is a method of counting bacteria by applying a coating of a specimen onto an agar plate, culturing for 18 to 24 h, and then counting the bacteria in the formed colony. In culturing methods, after the specimen coating is applied to a liquid medium and cultured, growth of the bacteria can be determined by the presence of a suspension.

The ATP assay method is a method of counting bacteria by extracting ATP, which represents bacterial activity, from a specimen, adding a luminous reagent to react with the ATP, and detecting the intensity of the light emitted by the luminous reagent.

The fluorescent assay method stains a specimen using a combination of a fluorescent dye to stain living bacteria and a fluorescent dye to stain dead bacteria, and detects and counts the living bacteria and the dead bacteria via a flow hyetometer and fluorescence microscope.

There are various problems associated with conventional methods, however. For example, the culturing method is basically performed manually, and requires complex operation. Since culturing takes a long time, considerable time must elapse before the bacteria can be counted. Furthermore, only cultural bacteria can be counted.

The ATP assay method requires complex preprocessing, such as the ATP extraction process. Since the bacteria are not counted directly, and the bacteria are counted based on ATP concentration from the intensity of light emission by the luminous reagent, there is a possibility for calculation errors. Furthermore, only bacteria that produce ATP can be counted.

Fluorescent assay requires two types of dyes, which have widely different detection wavelengths for the detection of living bacteria and the detection of dead bacteria, respectively. Accordingly, in order to count living bacteria and dead bacteria, the same sample must be measured using different detection devices for each dye, thereby complicating the structure of the assay device. In addition, the operation of the assay device also becomes complicated.

As described above, the conventional methods are disadvantageous in that they can only count living bacteria, are complicated to operate, or require complex measuring devices capable of counting living bacteria and dead bacteria.

When an antibiotic is added to the specimen containing the bacteria and the change in the number of bacteria is observed over time to determine the antibacterial effect, it is desirable to obtain not only the number of living bacteria, but also the number of dead bacteria. Furthermore, when confirming the presence of bacteria in a specimen beforehand, the bacteria must be counted and a culture study performed if the bacteria are alive, whereas a culture study is unnecessary when the bacteria are dead. Therefore it is desirable to obtain a live bacteria count from the specimen in order to determine whether or not a culture study is required.

European Patent publication No. 1 136 563 A2 describes a method for dying bacteria by applying a cationic surface-active agent to a specimen containing bacteria, then adding a dye. There is no mention of obtaining both a live bacteria count and a dead bacteria count.

In short, a simple method capable of providing both a live bacteria count and a dead bacteria count would be desirable.

SUMMARY

The scope of the present invention is defined solely by the appended claims, and is not affected to any degree by the statements within this summary.

A first method for counting bacteria embodying features of the present invention includes: (a) preparing an assay sample by staining a specimen using a fluorescent dye, thereby producing a difference in fluorescent intensity between live bacteria and dead bacteria; (b) detecting optical information from the assay sample; and (c) classifying and counting the live bacteria and the dead bacteria based on the detected optical information.

A second method for counting bacteria embodying features of the present invention includes: (a) preparing a first assay sample by dividing a specimen into at least two parts and staining a first specimen part using a first fluorescent dye, thereby producing a difference in fluorescent intensity between live bacteria and dead bacteria; (b) preparing a second assay sample by staining all bacteria in a second specimen part using a second fluorescent dye and a surface-active agent; (c) detecting a first optical information from the first assay sample; (d) detecting a second optical information from the second assay sample; (e) classifying and counting dead bacteria in the first assay sample based on the first optical information; (f) classifying and counting all bacteria in the second assay sample based on the second optical information; and (g) calculating a number of live bacteria based on a total bacteria count obtained from the second assay sample and a dead bacteria count obtained from the first assay sample.

A first bacteria counting apparatus embodying features of the present invention includes: (a) an assay sample preparation unit for preparing an assay sample by staining a specimen using a fluorescent dye, thereby producing a difference in fluorescent intensity between live bacteria and dead bacteria; (b) a detection unit for detecting optical information from the assay sample; and (c) an analysis unit for classifying and counting the live bacteria and the dead bacteria based on the optical information detected by the detection unit.

A second bacteria counting apparatus embodying features of the present invention includes: (a) an assay sample preparation unit comprising a sampling device for providing a first specimen and a second specimen from a specimen, the assay sample preparation unit for preparing a first assay sample by staining the first specimen using a first fluorescent dye, thereby producing a difference in fluorescent intensity between live bacteria and dead bacteria, and for preparing a second assay sample by staining all bacteria of the second specimen using a second fluorescent dye and a surface-active agent; (b) a detection unit for detecting a first optical information from the first assay sample and for detecting a second optical information from the second assay sample; and (C) an analysis unit for classifying and counting dead bacteria in the first assay sample based on the first optical information, for classifying and counting all bacteria in the second assay sample based on the second optical information, and for calculating a number of live bacteria based on a total bacteria count obtained from the second assay sample and a dead bacteria count obtained from the first assay sample.

A reagent kit for counting bacteria embodying features of the present invention includes: (a) a first dilution fluid substantially void of a surface-active agent; (b) a second dilution fluid comprising a surface-active agent; and (c) a stain comprising a fluorescent dye.

DETAILED DESCRIPTION

Figure 1:
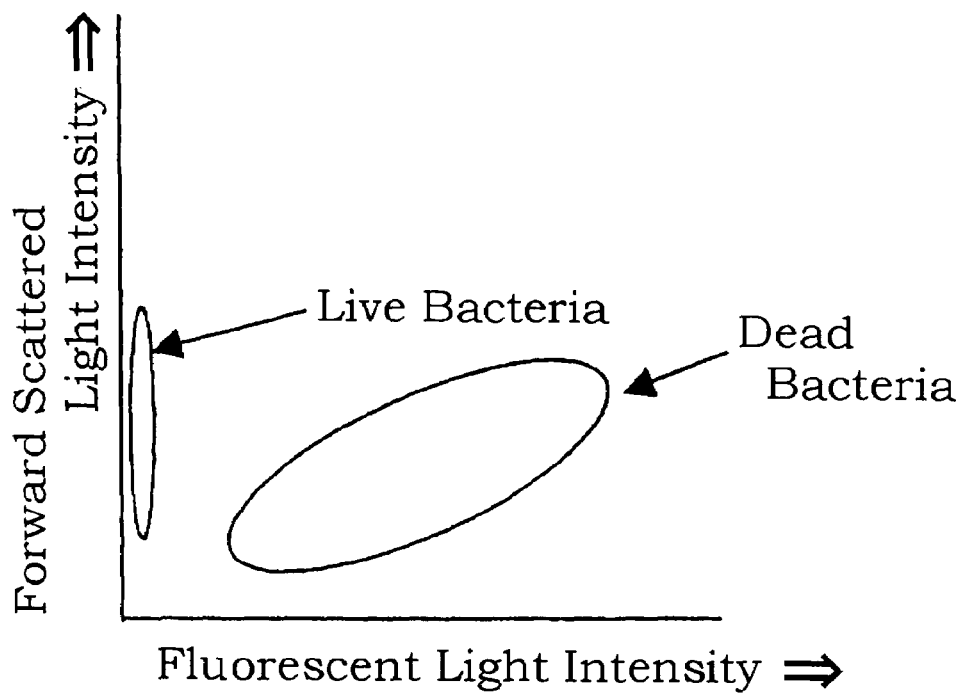
FIG. 1 is a diagram showing the position at which each bacterium appears when classified and counted by a method embodying features of the present invention.

The specimens used in accordance with the present invention include clinical specimens. Representative examples include but are not limited to urine, blood, spinal fluid, and the like, food and water, drinking water, and cultures thereof. The bacteria may be any bacteria that affect the human body or the environment, including but not limited to *E. coli, S. aurous, E. facials, S. marksmens, P. aerations,* and the like.

When processing a specimen with a fluorescent dye, it is desirable that the process be performed at a pH of between about 2.0 and about 4.5. For this reason, a buffer solution in the acidic pH range of approximately 2.0 to 4.5 may be used. Examples of useful acids include but are not limited to citric acid, phosphoric acid, ophthalmic acid, succinct acid, numeric acid, and the like. These acids may be used in any amount insofar as the aforesaid pH range is maintained; a concentration within the range of about 10 to about 500 mM is desirable. Examples of useful buffer solutions having an approximate pH in the range of about 2.0 to about 4.5 include but are not limited to Britton-Robinson buffer solution, Clark-Lubs buffer solution, Kolthoff buffer solution, McIlvaine buffer solution, Michaelis buffer solution, Sorensen buffer solution, and the like. In the above-mentioned pH range, nonspecific staining of material other than bacteria is suppressed compared to in neutral and alkaline pH.

The first fluorescent dye produces a difference in fluorescent intensity between live bacteria and dead bacteria, and desirably stains dead bacteria in the acidic region. Among such dyes, polymethine dyes are presently desirable. Representative polymethine dyes are shown in (1) to (11) below:

(1) Thizole orange

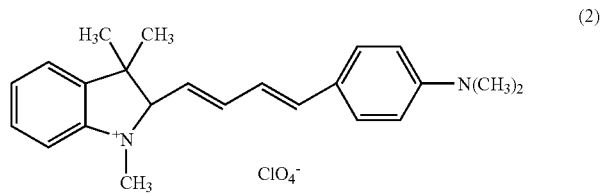

(2)

(3)

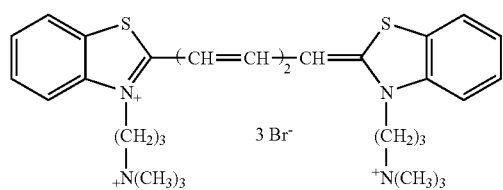

(4)

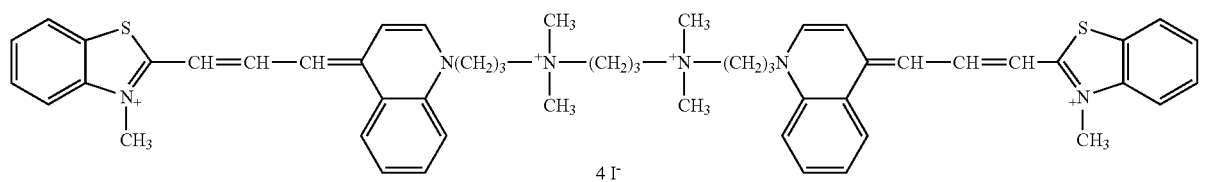

(5)

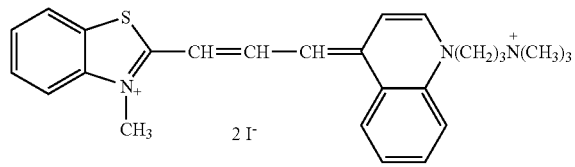 (6)

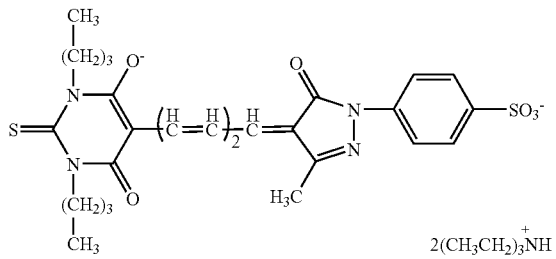 (7)

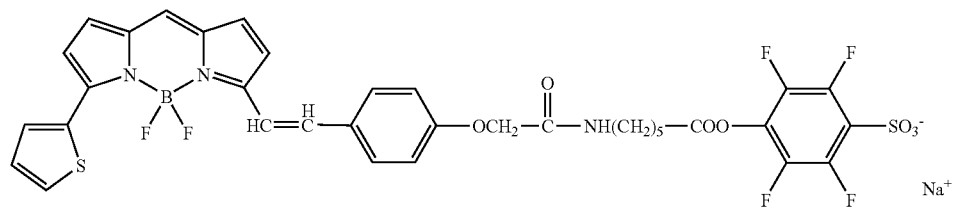 (8)

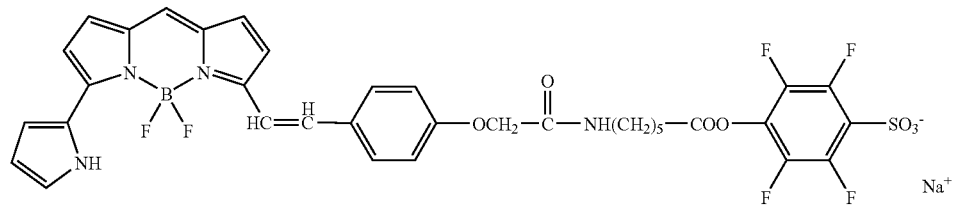 (9)

(10) Compounds having the general formula:

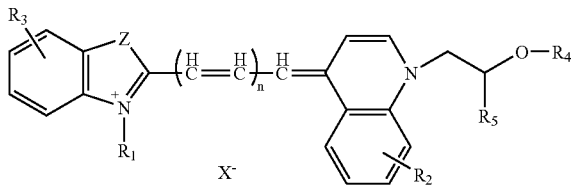

wherein, R1 represents a hydrogen atom or an alkyl group having 1 to 3 carbon atoms; R2 and R3 represent hydrogen atoms, alkyl groups having 1 to 3 carbon atoms, or alloy groups having 1 to 3 carbon atoms; R4 represents a hydrogen atom, acryl group, or alkyl group having 1 to 3 carbon atoms; R5 represents a hydrogen atom or alkyl group having 1 to 3 carbons atoms which may optionally be substituted; Z represents a sulfur atom, oxygen atom or carbon atom substituted by an alkyl group having 1 to 3 carbon atoms; n represents 1 or 2; and X represents an anion.

(11) Compounds having the general formula:

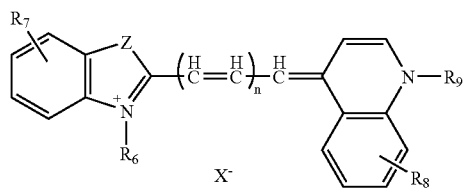

wherein, R6 represents a hydrogen atom or alkyl group having 1 to 18 carbon atoms; R7 and R8 represent hydrogen atoms, alkyl groups having 1 to 3 carbon atoms, or alkoxy groups having 1 to 3 carbon atoms; R9 represents a hydrogen atom, acyl group, or alkyl group having 1 to 18 carbon atoms; Z represents a carbon atom having an alkyl group with 1 to 3 carbon atoms, a sulfur atom, or an oxygen atom; n represent 0, 1, or 2; and X represents an anion.)

Examples of useful alkyl groups with 1 to 3 carbon atoms include but are not limited to methyl, ethyl, propyl, and the like. Examples of useful alkyl groups with 1 to 18 carbon atoms include but are not limited to methyl, ethyl, propyl, butyl, pentyl, hexyl, octyl, dodecyl, tetradecyl, and the like.

Examples of useful alloy groups with 1 to 3 carbon atoms include but are not limited to methoxy, ethoxy, propoxy, and the like.

Examples of useful acyl groups include but are not limited to: alkaloyls with 1 to 4 carbon atoms, such as formyl, acetyl, propionyl, butyryl and the like; alkenoyls with 3 to 18 carbon atoms, such as acryloyl, propyroyl, oleoyl, and the like; and aroyls with 7 to 11 carbon atom, such as benzoyl, toluoyl, xyloyl, naphthoyl, and the like.

Examples of useful anions include but are not limited to halogen ions such as fluorine, bromine, iodine, chlorine, and the like, and $ClO_4$, $BF_4$, and the like.

Among these dyes, (1) is commercially available, (2) and (3) are available from Japan Photosensitive Dye Research Center, and (5) through (9) are available from Molecular Probes, Inc. Dye (10) can be manufactured by the method described in U.S. Pat. No. 5,821,127. Dye (11) can be manufactured by the method described in U.S. Pat. No. 6,004,816.

Among the dyes represented by the general formula (10), the dye below is particularly desirable at present.

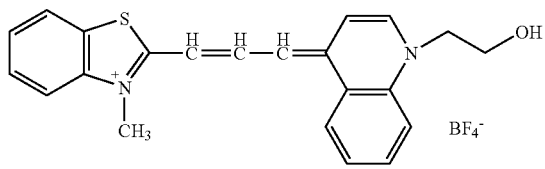

Regarding the concentration of the first fluorescent dye, although a suitable concentration will differ depending on the type of fluorescent dye, a concentration within a range of, for example, about 0.1 to about 100 ppm (final concentration) is presently desirable.

The processing of the specimen and the first fluorescent dye may be accomplished by mixing the specimen, dye, and a buffering agent. When mixing, a solvent may be added to the specimen, dye, and buffering agent as necessary to dilute or dissolve to a desired concentration. Furthermore, the mixing may be accomplished by adding solvent to one or more of the specimen, dye, and buffer so as to adjust the diluted, dissolved or suspended solution, followed by mixing the solution. Usable solvents include but are not limited to water and water-soluble organic solvents, such as ethanol, ethylene glycol, and the like. When the specimen is urine, staining by the fluorescent dye is inhibited by the influence of nitrous acid produced by some bacteria. In order to eliminate this influence, a nitrous acid reducing agent may be added in the processing of the specimen and first fluorescent dye. By way of example, amid sulfuric acid may be used as the nitrous acid reducing agent.

Although the temperature and duration of processing of the specimen and first fluorescent dye are not limited, a temperature of about 35 to about 50° C., and a duration of about 10 to about 30 seconds are presently desirable. The first assay sample can be prepared by this process.

The prepared first assay sample is exposed to light, and optical information including the fluorescent light and scattered light emitted from each bacterium stained by the fluorescent dye in the assay sample is detected. Scattered light includes lateral scattered light, forward scattered light, and the like. Fluorescent light includes lateral fluorescent light, forward fluorescent light, and the like. A flow hyetometer may be used to detect such optical information.

The dead bacteria and the live bacteria are classified and counted using the optical information thus obtained. Compared to dead bacteria, the material within live bacteria is resistant to fluorescent staining due to the action of the bacterial membrane. This fact is used in accordance with the present invention to process a specimen using a first fluorescent dye with the conditions that dead bacteria are subjected to adequate fluorescent staining, and live bacteria are subjected to either weak fluorescent staining or essentially fluorescent staining as compared to dead bacteria. In this way, a difference in the degree of staining arises between the live bacteria and the dead bacteria, such that a difference is produced in the intensity of fluorescent light detected from each bacterium.

When a difference is produced in the fluorescent light intensity of live bacteria and dead bacteria, the live bacteria, which have a low detected fluorescent light intensity, and the dead bacteria, which have a high detected fluorescent light intensity, can be clearly classified and detected as shown in FIG. 1. In this instance, the live bacteria and the dead bacteria can be classified and counted based on fluorescent light intensity alone. Regarding fluorescent light intensity, if the threshold value is set at a value higher than the fluorescent light intensity emitted by live bacteria and lower than the fluorescent light intensity emitted by dead bacteria, the bacteria with a fluorescent light intensity lower than the threshold value can be classified and counted as live bacteria, and the bacteria with a fluorescent light intensity higher than the threshold value can be classified and counted as dead bacteria. When fluorescent light intensity is used in this way, a histogram having fluorescent light intensity and number of bacteria as axes can be created instead of the two-dimensional scatter gram shown in FIG. 1. Moreover, the live bacteria and the dead bacteria can be classified and counted based upon this histogram.

Furthermore, live bacteria and dead bacteria can be classified and counted by combining the forward scattered light intensity and the fluorescent light intensity. This method can be used when it is difficult to adequately classify live bacteria and dead bacteria by fluorescent light intensity alone. If a scatter gram is created using forward scattered light intensity and fluorescent light intensity as the axes, as shown in FIG. 1, regions may be set so as to circumscribe the live bacteria population and the dead bacteria population. Then, the bacteria can be counted within each region to obtain the live bacteria count and the dead bacteria count.

In addition to the process described above, part of the same specimen is subjected to processing with a second fluorescent dye, depending on the type of specimen used and the type of bacteria contained in the specimen, such that the bacteria can be classified and counted with greater accuracy by calculating the total bacteria count.

The specimen processed with the second fluorescent dye is desirably divided into two parts beforehand, and one part is subjected to processing by the first fluorescent dye as described above, whereas the other part is subjected to processing using the second fluorescent dye.

The second fluorescent dye may be selected from among the above-described examples of first fluorescent dyes. The concentration of the second fluorescent dye is desirably substantially the same as that of the first fluorescent dye. The detection wavelengths of the first fluorescent dye and the second fluorescent dye are desirably detectable using the same detection device, and it is particularly desirable that the second fluorescent dye and the first fluorescent dye be identical.

In the process with the second fluorescent dye, it is desirable and important that a surface-active agent be used. Examples of useful surface-active agents include but are not limited to cationic surface-active agents, anionic surface-active agents, amphitricha surface-active agents, nonionic surface-active agents, and the like. The surface-active agent damages the cell membrane (cell wall) of the bacteria, such that the fluorescent dye can effectively enter into the bacteria, and thus generally stain the bacteria. Among these surface-active agents, cationic surface-active agents are presently desirable for their ability to effectively stain bacteria. Cationic surface-active agents can dissolve and contract viscous fibers present in the specimen, erythrocytes, cell fragments, and the like, and are therefore desirable for their superior effectiveness in preventing interference with the bacteria count.

Cationic surface-active agents are not limited, and useful examples include quaternary ammonium salts, such as shown in the formula below:

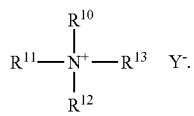

In this formula, R10 represents an alkyl group having 6 to 18 carbon atoms or (C₆H₅)—CH₂—; R11, R12, and R13 represent the same or different alkyl groups having 1 to 3 carbon atoms benzyl groups; and Y represents a halogen ion.

Examples of useful alkyl groups with 1 to 3 carbon atoms include but are not limited to methyl, ethyl, propyl, and the like. Examples of useful alkyl groups with 6 to 18 carbon atoms include but are not limited to hexyl, pentyl, octyl, decyl, dodecyl, tetradecyl, and the like. Examples of useful halogens include but are not limited to fluorine, bromine, iodine, chlorine, and the like.

Suitable ammonium salts include but are not limited to hexyltrimethyl ammonium salt, octyltrimethyl ammonium salt, decyltrimethyl ammonium salt, dodecyltrimethyl ammonium salt, tetradecyltrimethyl ammonium salt, hexadecyltrimethyl ammonium salt, octadecyltrimethyl ammonium salt, benzyltrimethyl ammonium salt, and the like.

Other examples of cationic surface-active agents include pyridinium salts shown by the formula:

[(C5H5)N⁺—(CH2)n-CH3]Y⁻.

In this formula, n represents 7 to 17; and Y represents a halogen ion.

Suitable pyridinium salts include but are not limited to octyl pyridinium salt, decal pyridinium salt, dodecyltrimethyl pyridinium salt, tetradecyltrimethyl pyridinium salt, hexadecyltrimethyl pyridinium salt, and the like.

Although the concentration of cationic surface-active agent will differ depending on the type used, the final concentration may be, for example, in a range of about 10 to about 50,000 mg/ml, and desirably, in a range of about 100 to about 3,000 mg/ml.

The anionic surface-active agent is not limited, and suitable examples include but are not limited to lauroylsarcosine acid salt as an N-acylaminoacetic acid salt, myristoylsarcosine acid salt, oleoylsarcosine acid salt, oleic acid salt, and the like.

Although the concentration of the anionic surface-active agent will differ depending on the type used, the final concentration may be, for example, in a range of about 0.1 to about 10 mg/ml, and desirably in a range of about 0.5 to about 5 mg/ml.

The amphitricha surface active agent is not limited, and a useful example includes the betaine acetate shown by the formula:

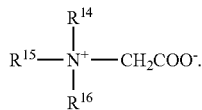

In this formula, R14 represents an alkyl group having 8 to 20 carbon atoms; R15 and R16 represent the same or different alkyl group having 1 to 3 carbon atoms, alkenyl groups or alkynyl groups having 2 to 3 carbons atoms.

The alkyl group with 1 to 3 carbon atoms may be the same as above. Examples of useful alkenyl groups with 2 to 3 carbons atoms include but are not limited to vinyl, ally, and the like. Examples of useful alkynyl groups with 2 to 3 carbon atoms include but are not limited to acetylene, propane, and the like. Examples of useful alkyl groups with 8 to 20 carbon atoms include but are not limited to octyl, decal, codicil, tetradecyl, and the like.

Examples of suitable betaine acetates include but are not limited to docecyldimethyl ammonium-betaine acetate, hexadecyldimethyl ammonium-betaine acetate, decyldimethyl ammonium-betaine acetate, lauryldimethyl ammonium-betaine acetate, and the like.

Although the concentration of the surface-active agent will differ depending on the type, a final concentration of, for example, about 1 to about 100 mg/ml may be used, with a final concentration of about 5 to about 20 mg/ml being presently desirable.

Nonionic surface-active agents are not limited, and suitable examples of polyoxyethylene(n)alkyl ethers desirably have an alkyl group with 10 to 20 carbon atoms, where n represents 10 to 20. Desirably, the polyoxyethylene(n)alkyl phenyl ethers have an alkyl group with 8 to 10 carbon atoms, where n represents 2 to 20 (e.g., POE (10)octylphenyl ethers, and the like).

Although the concentration of the nonionic surface-active agent will differ depending on the type, a final concentration of, for example, about 1 to about 100 mg/ml may be used, with a final concentration of about 5 to about 20 mg/ml being presently desirable.

Surface-active agents other than those described above, which are recognized as having properties that damage the cellular membrane of bacteria, include the materials below, which may be used as surface-active agents in accordance with the present invention: triton X-100 (polyethylene-glycol-mono[p-(1,1,3,3-tetramethylbutyl)phenyl]ether), CHAPS (3-[(3-chloroamidepropyl)diethylammonio]propane-sulfuric acid), CHAPSO (3-[(3-chloroamidepropyl)dimethylammonio]-2-hydroxypropane-sulfonic acid), BIG-CHAP (N,N-bis(3-D-gluconamidepropyl)chloramines), dioxy-BIGCHAP(N,N-bis(3-D-gluconamidepropyl)dioxychloramide), sucrose monocaprate, sucrose monochromatic, n-octyl-α-D-glucopyranoside, n-heptyl-α-D-thioglucopyranoside, n-octyl-α-D-thioglupyranoside, n-dodecyl-α-D-maltopyranoside, n-nonyl-α-D-thiomaltopyranoside, and the like.

Although the concentration of these surface-active agents will differ depending on the type, a final concentration of, for example, about 0.5 to about 50 mg/ml may be used, with a final concentration of about 1.0 to about 10 mg/ml being presently desirable.

The processing of the specimen and the second fluorescent dye can be performed by mixing the specimen, dye, surface-active agent, and buffering agent. When mixing, a solvent may be added to the specimen, dye, surface-active agent, and buffering agent as needed, so as to dilute or dissolve the material to a desired concentration. Furthermore, solvent may be independently added to one or more of the specimen, dye, surface-active agent, and buffering agent so as to adjust the diluted, dissolved or suspended solution, and the mixing may then be performed by mixing the solution. Useful solvents include but are not limited to water and water-soluble organic solvents, such as methanol, ethanol, ethylene glycol, and the like. When the specimen is urine, staining by the fluorescent dye is inhibited by the influence of nitrous acid produced by some bacteria. In order to eliminate this influence, a nitrous acid reducing agent may be added in the processing of the specimen and second fluorescent dye. By way of example, amid sulfuric acid may be used as the nitrous acid reducing agent.

Although the temperature and duration of processing of the specimen and second fluorescent dye are not limited, a temperature of about 35 to about 50° C., and a duration of about 30 seconds to about 10 minutes are desirable. The second assay sample can be prepared by this process.

Figure 2:
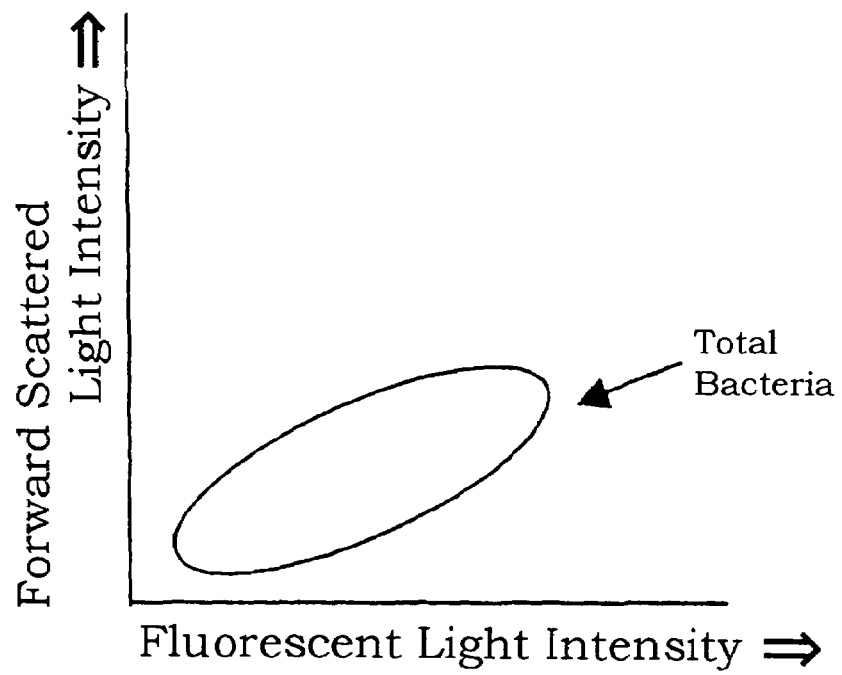
FIG. 2 is a diagram showing the position at which each bacterium appears when classified and counted by a method embodying features of the present invention.

The prepared second assay sample is exposed to light, and optical information including the fluorescent light and scattered light emitted from each bacterium stained by the fluorescent dye in the assay sample is detected in the same way as in the first assay sample. For example, the total bacteria are distributed, for example, in a scatter gram of forward scattered light intensity and fluorescent light intensity, as shown in FIG. 2. A region may be set so as to circumscribe the populations, such that a total bacteria count can be obtained by counting the bacteria within the region.

The live bacteria can be calculated by subtracting the dead bacteria count obtained from the first assay sample from the total bacteria count obtained from the second assay sample. Although the live bacteria can also be classified and counted from the first assay sample, impurities may be mixed in the range forming the population of live bacteria in the scatter gram, thus preventing an accurate live bacteria count. Regarding the same sample, it is more desirable to perform the calculation using the total bacteria count obtained from the second assay sample and the dead bacteria count obtained from the first assay sample, since an accurate live bacteria count can then be obtained.

The following examples and representative procedures illustrate features in accordance with the present invention, and are provided solely by way of illustration. They are not intended to limit the scope of the appended claims or their equivalents.

EXAMPLES

Composition of Dilution Fluid I (Without Surface-Active Agent)

| | |
|---|---|
| Citric acid | 100 mmol |
| Sodium sulfate | 90 mmol |
| Amidosulfuric acid | 100 mmol |
| NaOH | Sufficient to obtain a solution pH of 2.5 |
| Purified water | 1 liter |

Composition of Dilution Fluid II (with Surface-Active Agent)

| | |
|---|---|
| Citric acid | 100 mmol |
| Sodium sulfate | 90 mmol |
| Amidosulfuric acid | 100 mmol |
| NaOH | Sufficient to obtain a solution pH of 2.5 |
| Tetradecyltrimethyl Ammonium bromide | 1 g |
| Purified water | 1 liter |

Composition of Staining solution:
Fluorescent dye (structure below)—40 mg

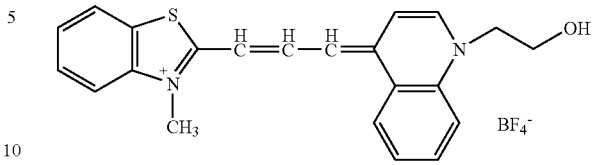

Ethylene glycol—1 liter

Bacteria Counting Apparatus

In the following examples 1 through 5, a bacteria counting apparatus in accordance with the present invention is described with reference to FIG. 3. This bacteria counting apparatus includes an assay sample preparation unit 1, a detection unit 2, and an analysis unit 3. The assay sample preparation unit 1 processes a specimen using a fluorescent dye and optional surface-active agent at a pH of about 2.0 to about 4.5 to prepare an assay sample. The assay sample preparation unit 1 includes a specimen suction pipette 6, a sampling valve 5, reaction chambers 14 and 15, dilution fluid containers 9 and 10, a stain container 8, suction pumps 4, 11, 12, and 13, and tubes connecting the various parts and flow control valves (not shown). The dilution fluid I is loaded in the first dilution fluid container 9, and the dilution fluid II is loaded in the second dilution fluid container 10. The stain is loaded in the stain container 8.

The operation of the bacteria counting apparatus in accordance with the present invention is described below. The operation of the bacteria counting apparatus includes an assay sample preparation process performed by the assay sample preparation unit 1, an optical information detection process performed by the detection unit 2, and an analysis process performed by the analysis unit 3. Each process is executed automatically.

Assay Sample Preparation Process

In the assay sample preparation unit 1, a specimen in a test tube 7 is first suctioned from the specimen suction pipette 6 via the operation of the suction pump 4. Then, the suctioned specimen is measured by the sampling valve 5, and supplied to the reaction chambers 14 and 15, respectively. Thus, a predetermined amount of specimen is allocated to the reaction chambers 14 and 15 from the same original specimen. The dilution containers 9 and 10 are respectively connected to the reaction chambers 14 and 15, such that the dilution fluid I is supplied to the first reaction chamber 14 and the dilution fluid II is supplied to the reaction chamber 15 through tubes via the respective suction pumps 12 and 13. The stain container 8 is connected to the reaction chambers 14 and 15, such that a predetermined amount of stain fluid containing fluorescent dye is supplied to the respective reaction chambers 14 and 15 through tubes via the suction pump 11. In the first reaction chamber 14, 50 μl of specimen, 340 μl of dilution fluid I, and 10 μl of stain are mixed in a bacteria staining process to prepare an assay sample. In the second reaction chamber 15, 50 μl of specimen, 340 μl of dilution fluid II, and 10 μl of stain are mixed in a bacteria staining process to prepare an assay sample. When only the assay sample prepared using the dilution fluid I is assayed, the specimen, dilution fluid II, and stain need not be supplied to the second reaction chamber 15. The assay samples prepared in each reaction chamber flow to a flow cell 16 of the detection unit 2 described below.

Optical Information Detection Process

Figure 4:
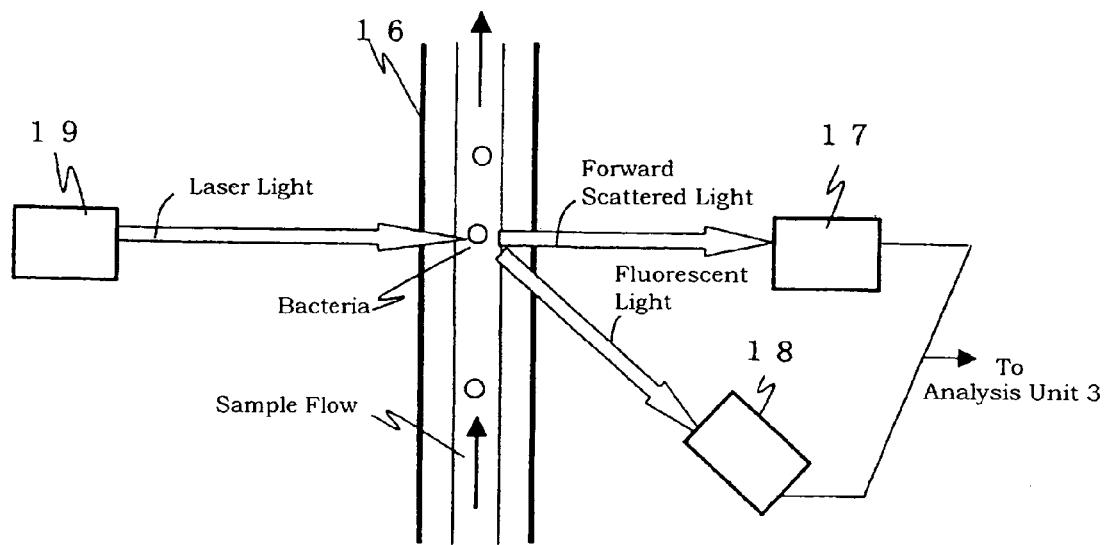
FIG. 4 is a schematic illustration depicting the operation of a bacteria counting apparatus embodying features of the present invention.

The detection unit 2 detects fluorescent light and scattered light optical information from each particle in the assay sample, and has the structure of the flow hyetometer shown in FIG. 4. The detection unit 2 is provided with a flow cell 16 for the flow of the assay samples, light source 19 for illuminating the assay sample flowing in the flow cell 16 with light, photomultiplier tube 18 for receiving the lateral fluorescent light emitted from the particles in the assay sample, and a photodiode 17 for receiving the forward scattered light. A red semiconductor laser light source emitting light at a wavelength of 630 nm is used in the light source 19. The photomultiplier tube 18 photo electrically converts (i.e., converts light to electrical signals) the detected lateral fluorescent light, and outputs the light as lateral fluorescent light signals. The photodiode 17 photo electrically converts the detected forward scattered light, and outputs the light as forward scattered light signals. These photo detection signals are transmitted to the analysis unit 3. In the detection unit 2 having the above-mentioned structure, fluorescent light and scattered light are generated to the degree that each particle included in the assay sample crosses the illumination region. of the laser light emitted by the light source 19. The lateral fluorescent light, which is received by the photomultiplier tube 18, and the forward scattered light, which is received by the photodiode 17, are subjected to photoelectric conversion, and output to the analysis unit 3 as optical detection signals (i.e., lateral fluorescent light signals and forward scattered light signals, respectively).

Analysis Process

The analysis unit 3 analyzes the optical detection signals of each particle detected by the detection unit 2, creates a two-dimensional scatter gram, and counts the bacteria. The analysis unit 3 includes a computer including CPU, ROM, RAM, and the like, and circuits for amplifying signals and eliminating noise. The analysis unit 3 analyzes the signal intensity obtained from the peak level of the optical detection signal pulse. The intensity of the fluorescent light signal represents the intensity of the fluorescent light detected from each particle, and is a parameter reflecting the degree of staining by the fluorescent dye. The intensity of the forward scattered light represents the intensity of the forward scattered light detected from each particle, and is a parameter reflecting the size of the particle. By combining these parameters, a two-dimensional scatter gram can be created, as shown in FIGS. 1 and 2. In the scatter grams, the number of bacteria is obtained by counting the blocks of particles appearing within regions set to correspond with the positions of appearance of, respectively, the live bacteria, dead bacteria, and all bacteria. The analysis unit 3 has an LCD display unit for displaying the scatter grams created for analysis and the results of the bacteria counts.

Examples 1 through 5 below were prepared using the dilution fluid I, dilution fluid II, and staining fluid having the above-described compositions, and a bacteria counting apparatus having the above-described structure. A summary of each example is provided below.

Example 1:

An assay sample I having a difference in fluorescent light intensity between live bacteria and dead bacteria contained in a specimen was prepared using the dilution fluid I and the staining fluid, and the sample was assayed to obtain a live bacteria count and a dead bacteria count.

Example 2:

An assay sample II in which all bacteria were fluorescently stained was prepared by processing the same specimen used in example 1 with the dilution fluid II (with surface-active agent) and the staining fluid, and the sample was assayed to obtain the total bacteria count. The live bacteria count was calculated by subtracting the dead bacteria count obtained in example 1 from the total bacteria count.

Example 3:

A specimen series of a mixture of fixed percentages of live bacteria and dead bacteria were assayed, and the method of calculating the live bacteria count by subtracting the dead bacteria count from the total bacteria count was used as in example 2. The detection accuracy was compared with that of conventional methods.

Example 4:

A predetermined amount of bacteria was added to a culture medium to which an antibiotic had been added, and the effectiveness of the antibiotic was tested by measuring the number of live bacteria in the medium over time. The live bacteria count was determined using the method of calculating the live bacteria count by subtracting the dead bacteria count from the total bacteria count in the same manner as in example 2.

Example 5:

A urine specimen was assayed using the method of calculating the live bacteria count by subtracting the dead bacteria count from the total bacteria count in the same manner as in example 2.

Example 1

Specimen Preparation

Pure cultures of *E. coli* and *S. aureus* were used, respectively, to a series of specimens 1 through 6 of mixtures containing fixed percentages of live bacteria and dead bacteria as shown in Table 1 below. The specimens were suspensions of bacteria in a hot infusion medium. In each series, the total bacteria count (100%) was approximately $10^5$ bacteria/ml (dead bacteria were prepared by processing live bacteria with alcohol, centrifuging, eliminating the supernatant, and adding to the fluid culture).

TABLE 1

|  | Live bacteria (%) | Dead bacteria (%) |
| --- | --- | --- |
| Series 1 | 100 | 0 |
| Series 2 | 80 | 20 |
| Series 3 | 60 | 40 |
| Series 4 | 40 | 60 |
| Series 5 | 20 | 80 |
| Series 6 | 0 | 100 |

Figure 3:
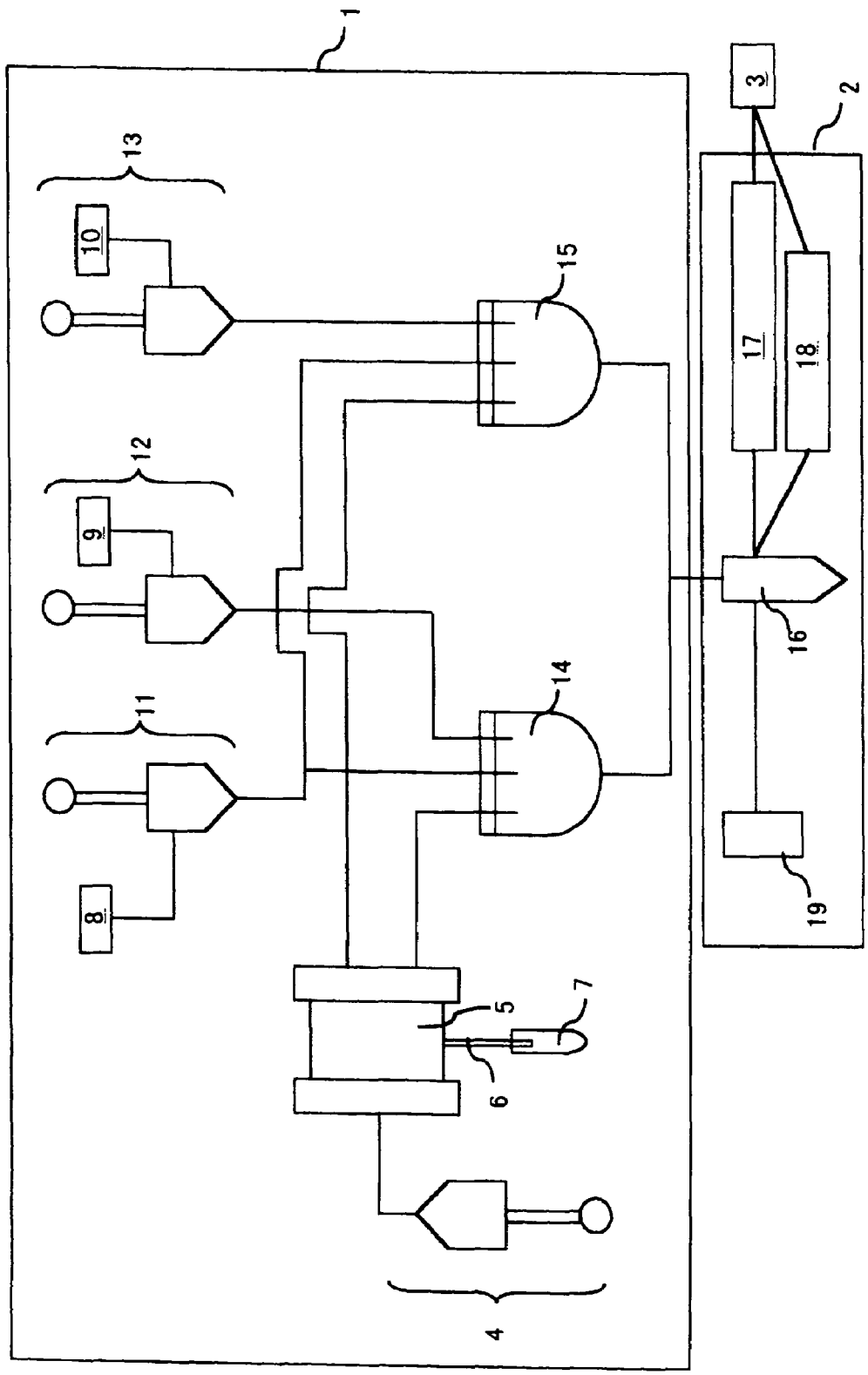
FIG. 3 is a schematic illustration of a bacteria counting apparatus embodying features of the present invention.

The specimen of *E. coli* series 4 was assayed using the apparatus shown in FIG. 3. In the reaction chamber 14 of the assay sample preparation unit 1, an assay sample I was prepared by processing the specimen, stain, and dilution fluid I at 40° C. for 10 seconds in the proportions shown below.

| | |
|---|---|
| Specimen | 50 μl |
| Dilution fluid I | 340 μl |
| Stain | 10 μl |
| Assay sample I | 400 μl |

Figure 5:
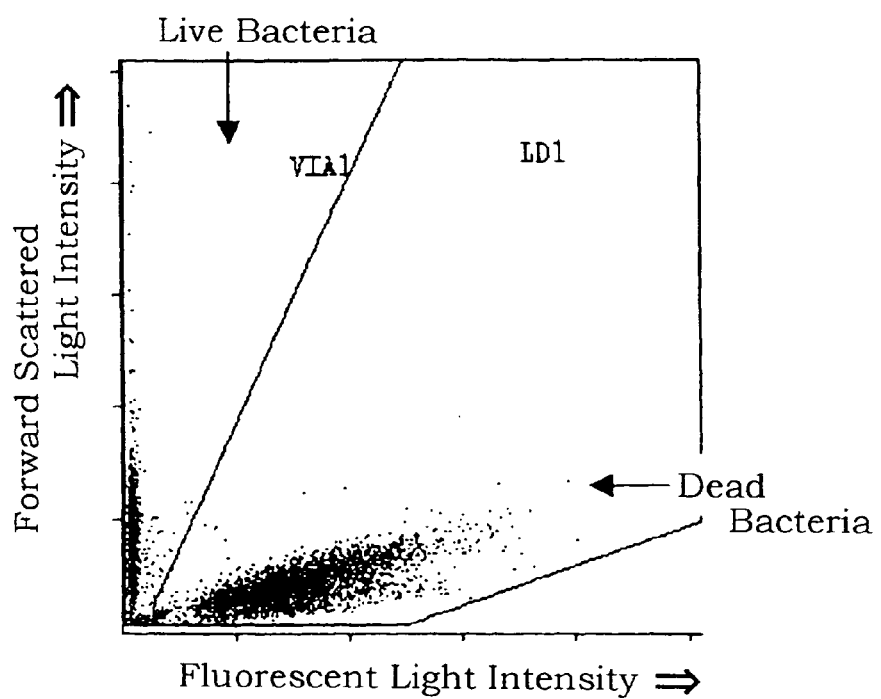
FIG. 5 shows a scatter gram obtained from an assay sample I in Example 1.

The forward scattered light signals and the lateral fluorescent light signals from the assay sample I are detected by the detection unit 2, and a two-dimensional scatter gram is created by the analysis unit 3 using the parameters of forward scattered light intensity and lateral fluorescent light intensity. On the scatter gram, regions which include the blocks of the live bacteria and dead bacteria are set, and the bacteria count in each sample is determined by counting the blocks in each region. The scattergram obtained from the assay sample I is shown in FIG. 5. In FIG. 5, region VIA1 is the region in which live bacteria appeared, and region LD1 is the region in which dead bacteria appeared. Although dead bacteria were adequately fluorescently stained with the staining fluid, the live bacteria were not actually stained by the fluorescent stain, such that live bacteria and dead bacteria respectively appeared as populations in the region VIA1 and region LD1 in each gating area.

The results of the classification and count of live bacteria and dead bacteria based on the scatter gram shown in FIG. 5 indicate the live bacteria population was $5.9 \times 10^5$ bacteria/ml, and the dead bacteria population was $7.1 \times 10^5$ bacteria/ml.

Assay by Other Methods (1) The specimen of *E. coli* series 4 was cultured using the agar culture method, and the live bacteria were counted. The live bacteria count thus obtained was $4 \times 10^5$ bacteria/ml.

(2) The specimen of *E. coli* series 4 was stained with fluorescent dye for total bacteria and dead bacteria using a Baclight L-7012 staining kit manufactured by Molecular Probes, Inc.. Then, the series 4 specimen was assayed using a commercial flow hyetometer (FACS Calibur; Becton-Dickinson, Inc.). The Baclight L-7012 is a kit which includes a green fluorescent dye for total bacteria count, and a red fluorescent dye for dead bacteria count. The live bacteria counts (obtained by subtracting the dead bacteria count from the total bacteria count) and the dead bacteria counts were $6 \times 10^5$ bacteria/ml and $8 \times 10^5$ bacteria/ml, respectively.

The live bacteria count and the dead bacteria count obtained by the methods embodying features of the present invention using the same specimen closely matched the live bacteria and dead bacteria counts obtained by the other methods.

Example 2

Among the specimens prepared in example 1, the specimen of *E. coli* series 4 was assayed using the apparatus shown in FIG. 3. In the second reaction chamber 15 of the assay sample preparation unit 1, an assay sample II was prepared by processing the specimen, stain, and dilution fluid II at 40° C. for 30 seconds in the proportions shown below.

| | |
|---|---|
| Specimen | 50 μl |
| Dilution fluid II | 340 μl |
| Stain | 10 μl |
| Assay sample II | 400 μl |

Figure 6:
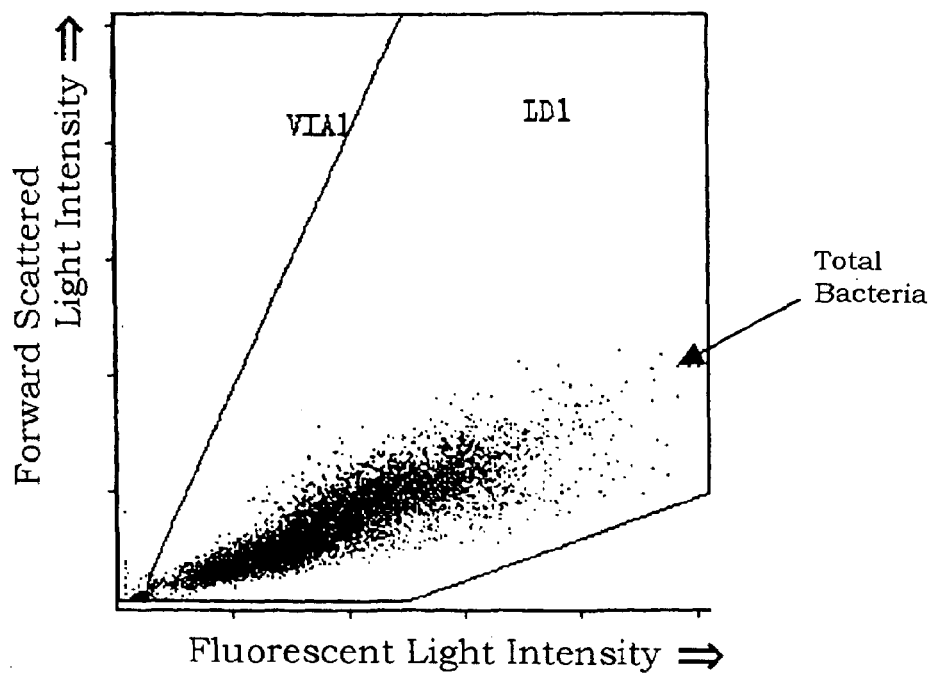
FIG. 6 shows a scatter gram obtained from an assay sample II in Example 2.

A scatter gram was created based on the forward scattered light intensity and the lateral fluorescent light intensity obtained from the assay sample II, as shown in FIG. 6, in the same manner as in example 1. In the scatter gram of FIG. 6, the region in which all bacteria appeared was set at the same position as the region of dead bacteria in the scatter gram of FIG. 5 (i.e., the region LD1). The total bacteria were counted using this scatter gram. The total bacteria count was $1.3 \times 10^6$ bacteria/ml. When the dead bacteria count obtained from FIG. 5 was subtracted from this total bacteria count, a live bacteria count of $5.9 \times 10^5$ bacteria/ml was obtained. This live bacteria count agreed well with the live bacteria count obtained from the scatter gram of FIG. 5 and the live bacteria count obtained by the other methods.

Example 3

Figure 7A:
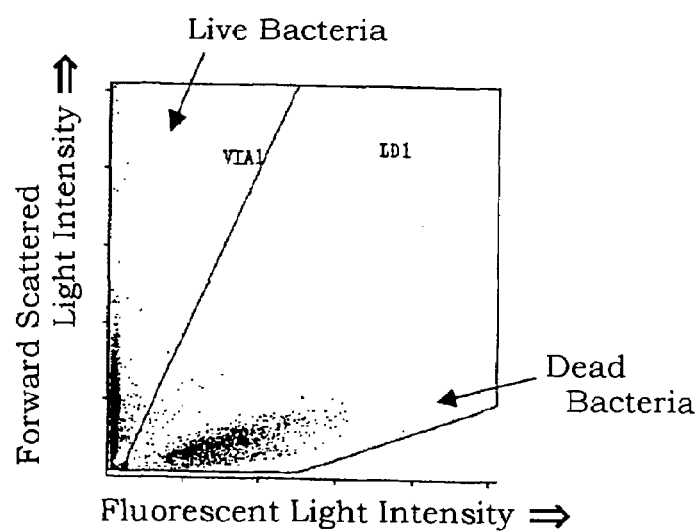
FIG. 7 shows a scatter gram obtained from an *E. coli* series in Example 3.
Figure 7B:
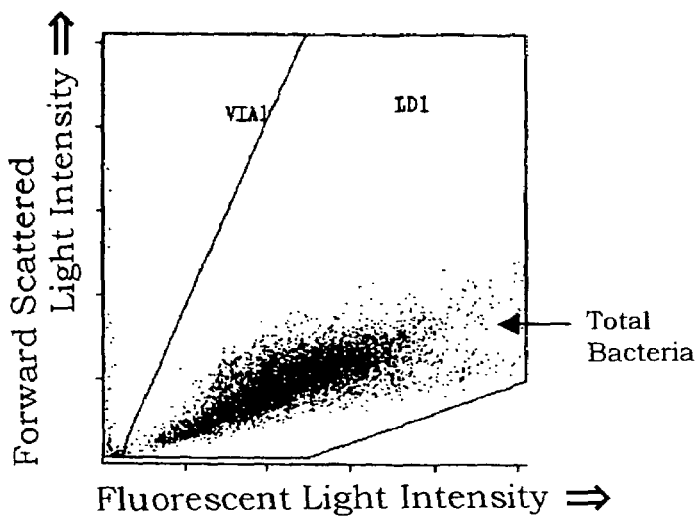
Figure 7C:
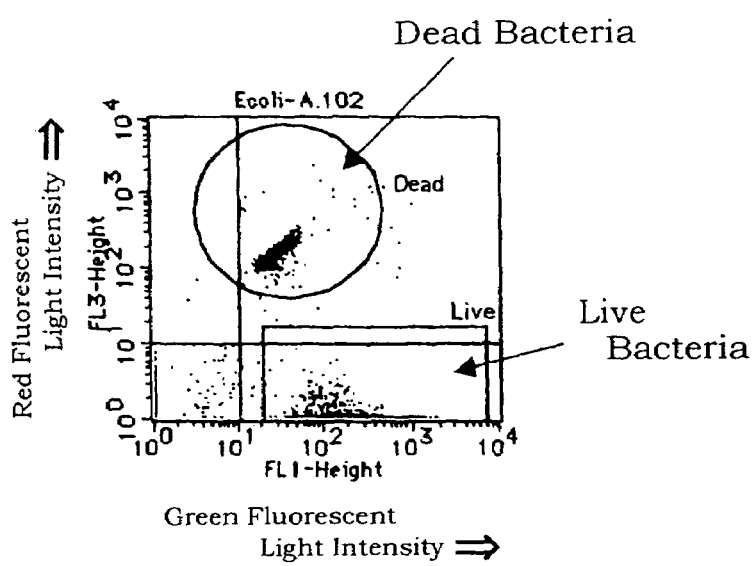
Figure 8A:
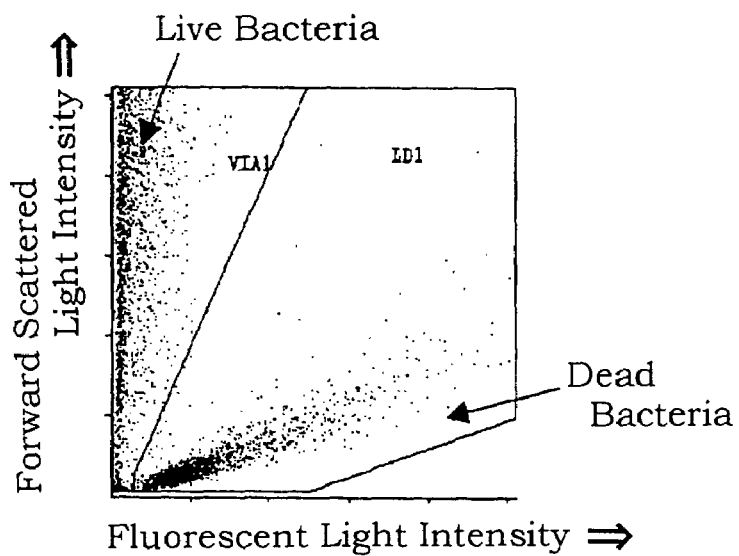
FIG. 8 shows a scatter gram obtained from an *S. aurous* series in Example 3.
Figure 8B:
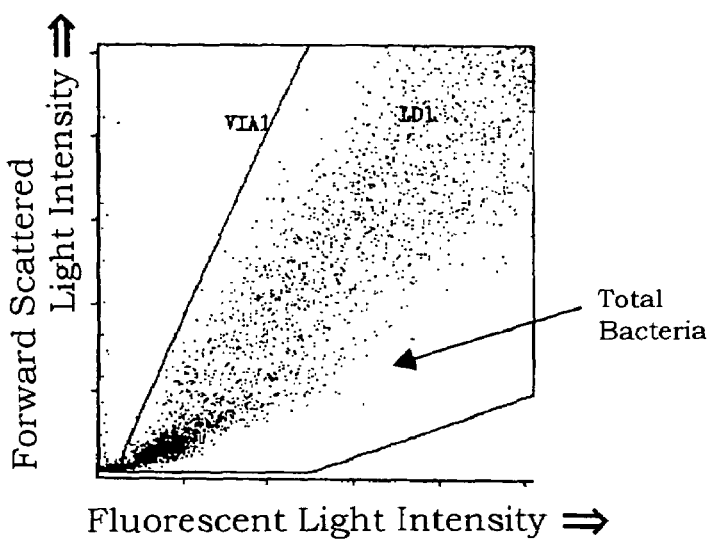
Figure 8C:
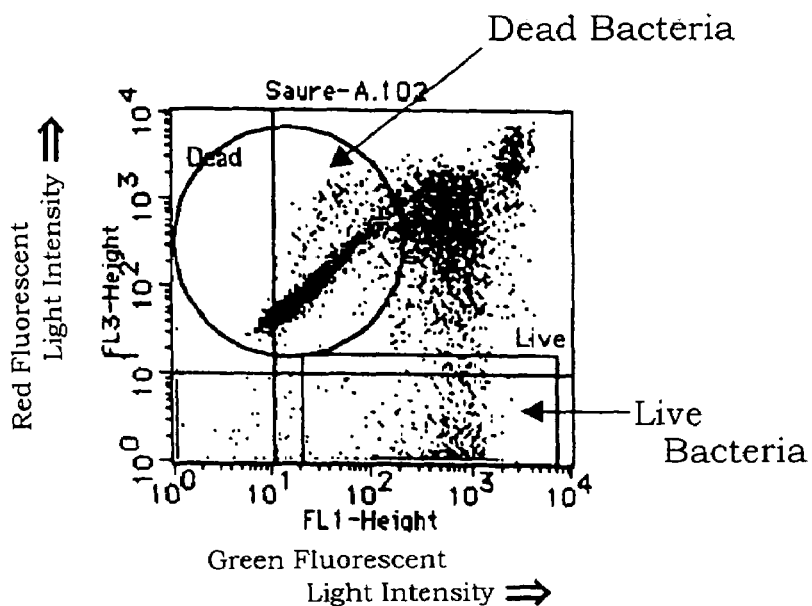
Figure 9A:
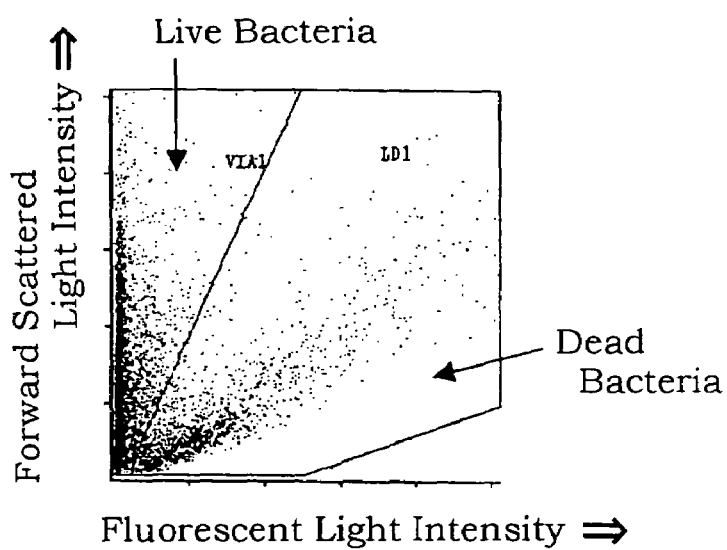
FIG. 9 shows a scatter gram obtained from an *E. facials* series in Example 3.
Figure 9B:
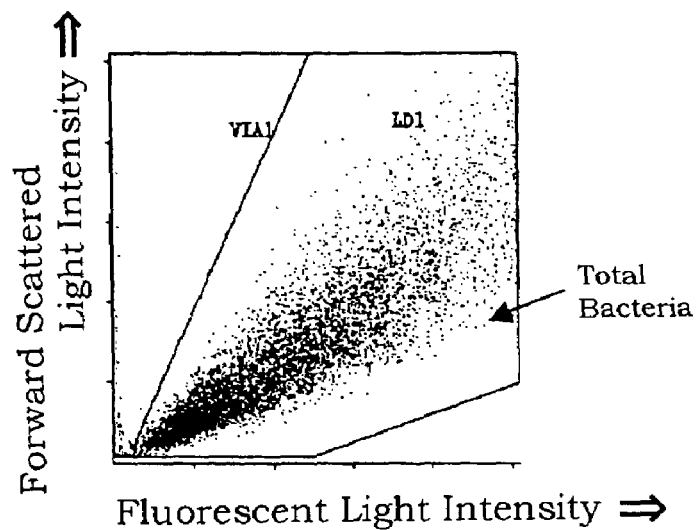
Figure 9C:
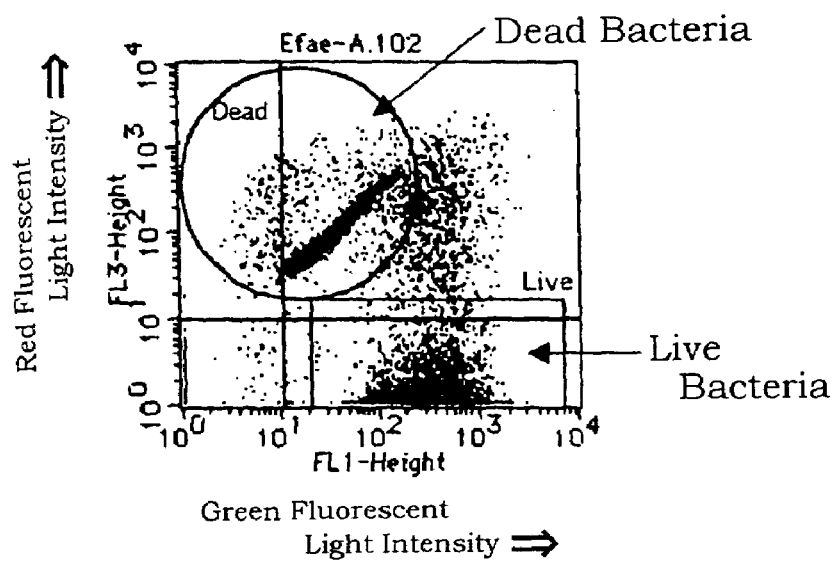

The specimens of *E. coli*, *S. aurous*, and *E. facials* of series 1 through 6 prepared in example 1 were processed with stain and dilution fluid I in the same manner as in example 1 to obtain an assay sample I, and processed with stain and dilution fluid II in the same manner as in example 2 to obtain an assay sample II. These assay samples were assayed in the same manner as in examples 1 and 2, and scatter grams were created. The scatter grams for series 2 are shown in FIGS. 7 through 9. *E. coli* is shown in FIGS. 7A, 7B, and 7C. *S. aurous* is shown in FIGS. 8A, 8B, and 8C. *E. facials* is shown in FIGS. 9A, 9B, and 9C.

In FIGS. 7 through 9, FIGS. 7A, 8A, and 9A were obtained by the method of the present invention using assay sample I. In the drawing, the region marked VIA1 is the region in which live bacteria appeared, and the region marked LD1 is the region in which dead bacteria appeared. In FIGS. 7 through 9, FIGS. 7B, 8B, and 9B were obtained by the method of the present invention using assay sample II. The region marked LD1 is the region in which all bacteria appeared. In FIGS. 7 through 9, FIGS. 7C, 8C, and 9C were obtained by subjecting the same sample to a staining process using the Baclight L-7012 staining kit (Molecular Probe, Inc.), and measuring the bacteria using a commercial flow hyetometer (FACS Calibur; Becton-Dickinson, Inc.). The vertical axis shows the intensity of the red fluorescent light detected from dead bacteria, and the horizontal axis shows the intensity of the green fluorescent light detected from the total bacteria.

Figure 10C:
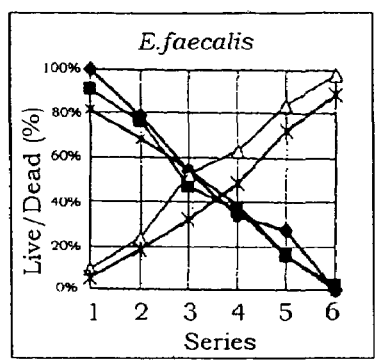
FIG. 10 shows graphs of the percentages of live bacteria and dead bacteria in a specimen obtained from Example 3 as counted by the various methods indicated.

The live bacteria count and the dead bacteria count in each specimen were obtained by analyzing each scatter gram as described in example 2 (the live bacteria count was calculated by subtracting the dead bacteria count from the total bacteria count). Graphs showing the obtained percentages of live bacteria and dead bacteria in each specimen are shown in FIGS. 10A, 10B, and 10C. FIG. 10A shows *E. coli*, FIG. 10B shows *S. aurous*, and FIG. 10C shows *E. facials*. The percentages of live bacteria obtained from the same specimens via the agar culture method are shown in the same graphs.

The percentages of live bacteria measured by the methods embodying features of the present invention closely matched the percentages of live bacteria in each series calculated using the agar culture method. However, the percentage of live bacteria measured using the Baclight kit differed from the totals obtained by the Backlight kit in the case of *S. aurous*.

Example 4

(1) A measured amount (approximately $10^5$ bacteria/ml) of bacteria (*E. coli*) was added to a cationic Muller-Hinton fluid medium with a fixed amount of antibiotic (ABPC 8 µg/ml).

(2) As a bacteria proliferation control, a fluid culture (without antibiotic) was prepared and the same amount of bacteria was added as in (1) above.

(3) The mediums of (1) and (2) were cultured at 35° C.

(4) Specimens were collected from cultures (1) and (2) immediately after adding the bacteria (0 h), and 2 h, 4 h, and 24 h after starting the cultures. Then, each specimen was assayed by the processes described below using the apparatus shown in FIG. 3.

| Process of specimen from culture (1) | |
| --- | --- |
| Specimen of culture (1) | 50 µl |
| Dilution fluid I | 340 µl |
| Stain | 10 µl |
| Assay sample I | 400 µl |
| (Reacted for 10 seconds at 40° C.) | |
| Specimen of culture (1) | 50 µl |
| Dilution fluid II | 340 µl |
| Stain | 10 µl |
| Assay sample II | 400 µl |
| (Reacted for 30 seconds at 40° C.) | |
| Process of specimen from culture (2) | |
| Specimen of culture (2) | 50 µl |
| Dilution fluid II | 340 µl |
| Stain | 10 µl |
| Assay sample III | 400 µl |
| (Reacted for 30 seconds at 40° C.) | |

The forward scattered light intensity and lateral fluorescent light intensity were detected from the assay samples I, II, and III in the same manner as in examples 1 and 2, and the number of bacteria were counted. The dead bacteria count was obtained from the scatter gram obtained from assay sample I, and the total bacteria count was obtained from the scatter grams of assay sample II and assay sample III. The live bacteria count was obtained by subtracting the dead bacteria count from the total bacteria counts of assay samples II and III.

Furthermore, a live bacteria count was obtained by measuring the specimen obtained from culture (1) via the agar culture method as a comparison with the methods embodying features of the present invention. In addition, the specimen obtained from culture (1) was processed with the Baclight L-7012 staining kit (Molecular Probe, Inc.), and the live bacteria were counted using a commercial flow hyetometer (FACS Calibur; Becton-Dickinson, Inc.).

Figure 11:
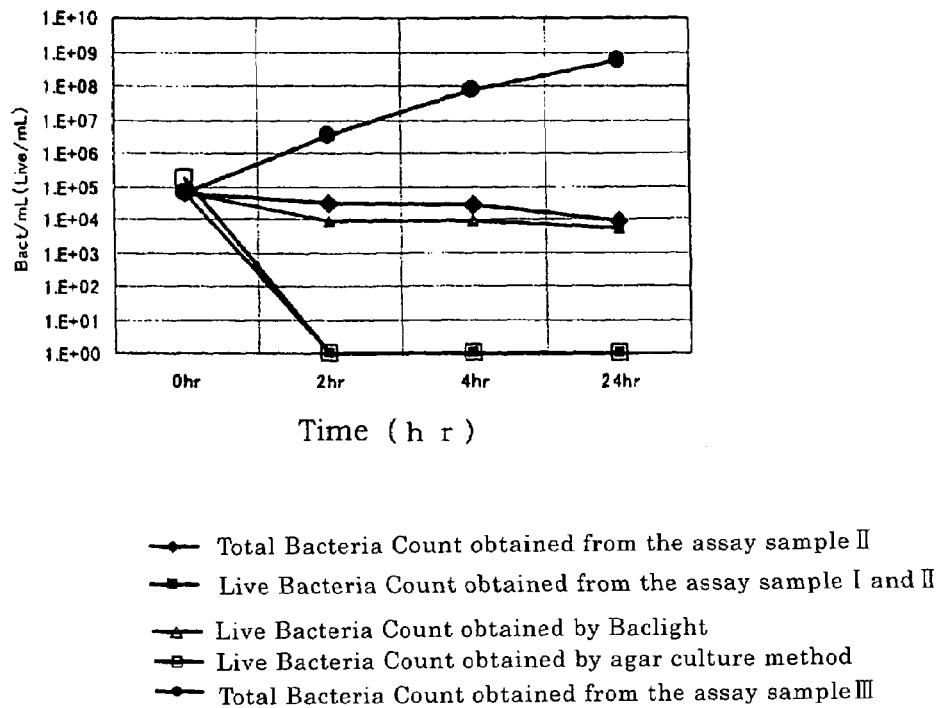
FIG. 11 is a graph of the number of bacteria obtained from Example 4 as counted by the various methods indicated.

The results obtained are shown in the graph of FIG. 11. As shown in FIG. 11, assay sample III, which did not have added antibiotic, had an increase in total number of bacteria. However, the live bacteria count obtained from the agar culture method showed a marked decrease in the live bacteria count 2 h and more after an antibiotic was added. The total bacteria count, after antibiotic was added, obtained from the assay sample II by the methods embodying features of the present invention was approximately fixed, and did not reflect a decrease in the number of live bacteria. However, the live bacteria count, after antibiotic was added, obtained from assay samples I and II by the methods embodying features of the present invention closely agreed with the live bacteria count obtained by the agar culture method, and indicates that the efficacy of antibiotics can be investigated using methods embodying features of the present invention.

Example 5

Urine Specimen Assay

Figure 12:
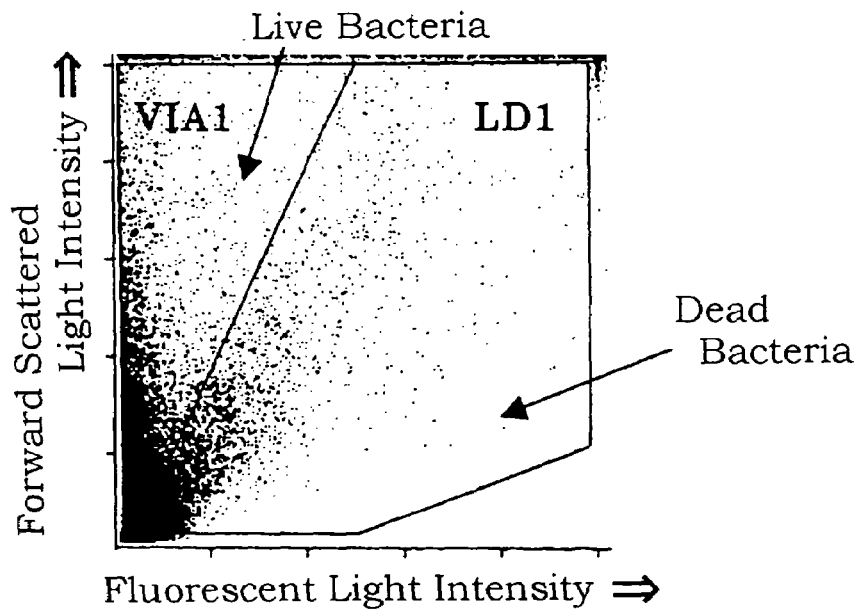
FIG. 12 shows a scatter gram obtained from an assay sample I in Example 5.
Figure 13:
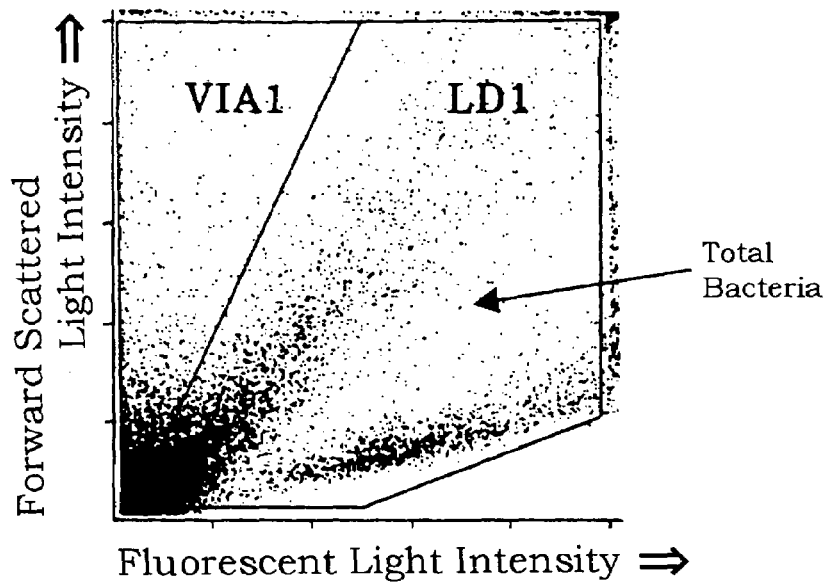
FIG. 13 shows a scatter gram obtained from an assay sample II in Example 5.

A urine specimen was assayed using the bacteria counting apparatus shown in FIG. 3. Using the dilution fluids I and II and stain in the same manner as in examples 1 and 2, an assay sample I processed by the dilution fluid that did not contain surface-active agent, and an assay sample II processed by the dilution fluid containing surface-active agent, were prepared and assayed. The scatter gram obtained from the assay of the assay sample I is shown in FIG. 12. In FIG. 12, the VIA1 region is the region in which live bacteria appeared, and the LD1 region is the region in which dead bacteria appeared. The scatter gram of the assay sample II is shown in FIG. 13. The LD1 region is the region in which total bacteria appear. In both cases, the vertical axis represents the forward scattered light intensity, and the horizontal axis represents the lateral fluorescent light intensity. Example 5 includes impurities in the specimen, such as debris (e.g., cell residues of leukocytes and the like) and viscous fibers, because the results are for the assay of an actual urine sample. Therefore, in the scatter gram of FIG. 12, impurities appear in the VIA1 region in which the live bacteria appeared, such that it is difficult to calculate an accurate live bacteria count from the scattergram of FIG. 12 using the analysis method of example 1. The number of bacteria was determined by the analysis method of example 2 using the scatter gram of FIG. 13. A dead bacteria count of $3.8 \times 10^5$/ml was obtained from the scattergram of FIG. 12. A total bacteria count of $6.8 \times 10^5$/ml was obtained from the scatter gram of FIG. 13. Therefore, a live bacteria count of $3.0 \times 10^5$/ml was obtained by subtracting the dead bacteria count obtained from the scatter gram of FIG. 12 from the total bacteria count obtained from the scattergram of FIG. 13.

Figure 14:
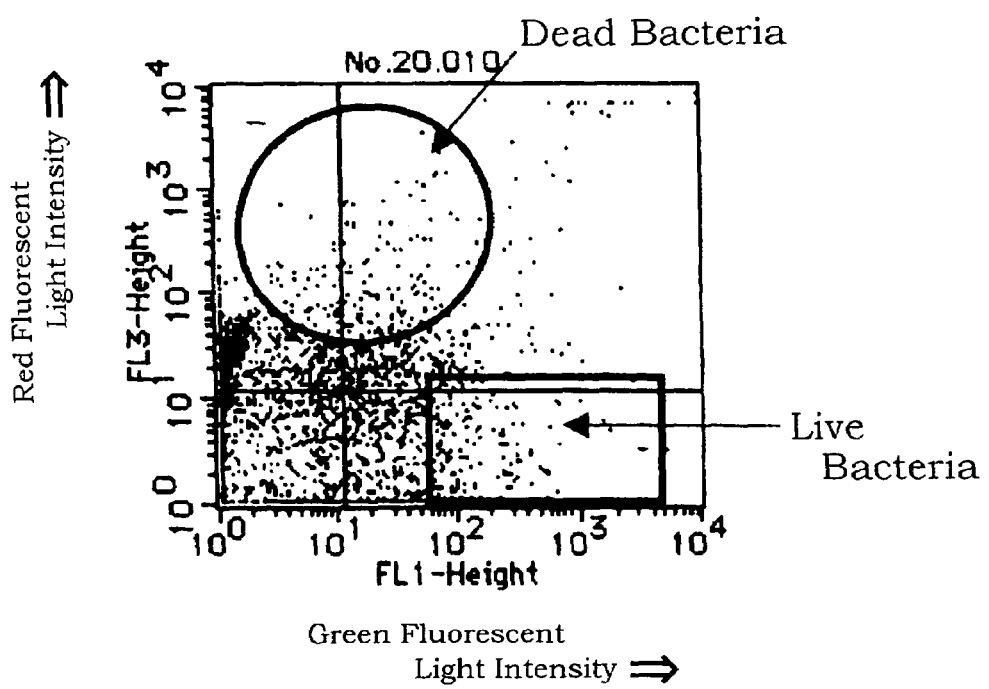
FIG. 14 shows a scatter gram obtained from a specimen stained with Baclight in Example 5.

As a control, the same urine specimen was processed by the Baclight L-7012 staining kit (Molecular Probes, Inc.) and assayed using a commercial flow hyetometer (FACS Calibur; Becton-Dickinson, Inc.). The scatter gram thus obtained is shown in FIG. 14. The vertical axis represents the intensity of the red fluorescent light detected from the dead bacteria, and the horizontal axis represents the intensity of the green fluorescent light detected from all bacteria. In this scatter gram, the stained bacteria did not form well-defined populations, and the live bacteria and dead bacteria could not be classified and counted. This is thought to have been a result of staining impurities other than the bacteria contained in the urine specimen.

When the same urine sample was assayed by the agar culture method as a control, the live bacteria count was $2.7 \times 10^5$/ml. This result indicates that the methods and apparatuses embodying features of the present invention produce a live bacteria count near that produced by the agar culture method even when the detection object is not a refined specimen, as in the case of a urine specimen.

The present invention counts live bacteria and dead bacteria in a specimen by measuring at a single wavelength. Since a total bacteria count can be determined by a method using a surface-active agent, the dead bacteria count obtained before, and a live bacteria count obtained from the total bacteria count, can be obtained with greater accuracy. Therefore, it is possible to rapidly confirm the bactericidal effectiveness of antibiotics, and the bactericidal process effectiveness of foods. Furthermore, since it is possible to detect bacteria more quickly than by conventional techniques, the need for culture studies can be quickly determined in the case of clinical specimens, and the like. In addition, preprocessing of specimens is simple, and the sequence of processes including detecting optical information from prepared assay samples through analysis can be completely automated, such that operator technique skill or method will not influence the assay result.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A method for counting bacteria in a clinical specimen that comprises Gram positive and Gram negative bacteria, the method comprising:

preparing a first assay sample by dividing the clinical specimen into at least two parts and staining a first specimen part using a fluorescent dye, thereby producing a difference in fluorescent intensity between live bacteria and dead bacteria;

preparing a second assay sample by staining all bacteria in a second specimen part using said fluorescent dye and a surface-active agent;

detecting a first optical information from the first assay sample;

detecting a second optical information from the second assay sample;

classifying and counting dead bacteria in the first assay sample based on the first optical information;

classifying and counting total bacteria in the second assay sample based on the second optical information; and calculating the number of live bacteria based on a total bacteria count obtained from the second assay sample and the dead bacteria count obtained from the first assay sample.

2. The method of claim 1, wherein-the said fluorescent dye comprises a polymethine dye.

3. The method of claim 1, wherein the surface-active agent comprises a cationic surface-active agent.

4. The method of claim 1, wherein the staining is performed at a pH of between about 2.5 and about 4.5.

5. The method of claim 1, wherein the first optical information and the second optical information comprise fluorescent light.

6. The method of claim 1, wherein the first optical information comprises fluorescent light and scattered light, and wherein the second optical information comprises fluorescent light and scattered light.

7. The method of claim 1, wherein the preparing of the second assay sample comprises damaging a cell membrane of the bacteria with the surface active agent to stain dead and live bacteria with said fluorescent dye.

8. The method of claim 1, wherein the first optical information and the second optical information are detected by using a flow cytometer.

9. The method of claim 1, wherein the dead bacteria are stained more strongly than the live bacteria in the preparing of the first assay sample.

* * * * *